(12) United States Patent
Thompson (10) Patent No.: US 6,638,920 B2
(45) Date of Patent: Oct. 28, 2003

(54) COMPOSITIONS AND METHODS OF PREVENTING OR REDUCING THE RISK OR INCIDENCE OF SKELETAL INJURIES IN HORSES

(75) Inventor: Donald R. Thompson, Annandale, NJ (US)

(73) Assignee: Merck & Co., Inc., Rahway, NJ (US)

( * ) Notice: Subject to any disclaimer, the term of this patent is extended or adjusted under 35 U.S.C. 154(b) by 12 days.

(21) Appl. No.: 09/902,913

(22) Filed: Jul. 11, 2001

(65) Prior Publication Data

US 2002/0033144 A1 Mar. 21, 2002

Related U.S. Application Data (60) Provisional application No. 60/219,668, filed on Jul. 21, 2000.

(51) Int. Cl.$^7$ .............................................. A61K 31/66
(52) U.S. Cl. ....................................................... 514/108
(58) Field of Search ......................................... 514/108

(56) References Cited

U.S. PATENT DOCUMENTS

| | | | |
|---|---|---|---|
| 3,962,432 A | 6/1976 | Schmidt-Dunker | |
| 4,621,077 A | 11/1986 | Rosini et al. | |
| 5,358,941 A | 10/1994 | Bechard et al. | |
| 5,994,329 A | 11/1999 | Daifotis et al. | |
| 6,057,306 A | 5/2000 | Wilson et al. | |
| 6,416,737 B1 * | 7/2002 | Manolagas et al. | 424/9.2 |

FOREIGN PATENT DOCUMENTS

| | | |
|---|---|---|
| WO | WO 97/12619 | 4/1997 |
| WO | WO 00/28954 | 5/2000 |

OTHER PUBLICATIONS

Mundy, Proc. Annual Conference of American Association of Equine Practioners (1997), pp. 204–210.

Hoekstra et al., Association for Equine Sports Medicine Proceedings, AGM, "Stalling young horses alters normal bone growth", Leesburg, VA (1998), pp. 11–14.

Estberg et al., J. of Amer. Veter. Med. Assoc., vol. 212(4) (1998), pp. 544–549, "Relationship between race start characteristics and risk of catastrophic injury in Thoroughbreds: 78 cases (1992)".

Carrier et al., J. of Amer. Veter. Med. Assoc., vol. 212(10) (1998), pp. 1582–1587, "Association between long periods without high–speed workouts and risk of complete humeral or pelvic fracture in Thoroughbred racehorses: 54 cases (1991–1994)".

Buckingham et al., Veterinary Record, vol. 128 (1991), pp. 370–373, "Osteopenic effects of forelimb immobilisation in horses".

Johnson et al., Equine Veterinary Journal, vol. 26(4), p. 327–330, "Causes in death in racehorses over a 2 year period".

Porr et al. J. of Animal Science, vol. 76 (1998), pp. 1875–1879, "Deconditioning reduces mineral content of the third metacarpal bone in horses".

Estberg et al., J. of Amer. Veter. Med. Assoc., vol. 208(1) (1996), pp. 92–96, "Fatal musculoskeletal injuries incurred during racing and training in Thoroughbreds".

Estberg et al., Amer. J. of Veter. Research, vol. 57(11) (1996), pp. 1549–1555, "High–speed exercise history and catastrophic racing fracture in Thoroughbreds".

Lepage et al., Ann. Med. Vet., vol. 132 (1988), pp. 391–399, "L'emploi d'un bisphosphonate (APD) dans la prevention des exostoses chez le poney Shetland. Etude preliminaire."

Lepage et al., Ann. Med. Milit. Belg., vol. 3(2) (1989), pp. 38–44, "Aspects microradiographiques et en microscopic de fluorescence d'une exostose experimentale du metcarpien chez le poney Shetland et de son traitement par un bisphosphonate, L'AHPrBP (APD) . . .".

Estberg et al., Preventative Vet. Med., vol. 33 (1998), p. 159–170, "A case–crossover study of intensive racing and training schedules and risk of catastrophic musculoskeletal injury and lay–up in California Thoroughbred racehorses".

* cited by examiner

*Primary Examiner*—Theodore J. Criares
(74) *Attorney, Agent, or Firm*—Nicole M. Wallinger; Mark R. Daniel (57) ABSTRACT

The present invention relates to compositions and methods of preventing or reducing the risk or incidence of skeletal injuries in horses. The present invention further relates to compositions and methods for alleviating pain associated with skeletal injuries in horses and to treating skeletal injuries in horses.

22 Claims, 4 Drawing Sheets

FIG. 4

Figure 4: Ultrasound measurements of calcaneous (percent change from baseline (mean +/-SE) of untreated and alendronate treated horses

*p = 0.08

COMPOSITIONS AND METHODS OF PREVENTING OR REDUCING THE RISK OR INCIDENCE OF SKELETAL INJURIES IN HORSES

CROSS REFERENCE TO RELATED APPLICATIONS

The present application claims priority of U.S. provisional application Ser. No. 60/219,668, filed Jul. 21, 2000.

FIELD OF THE INVENTION

The present invention relates to compositions and methods for preventing or reducing the risk or incidence of skeletal injuries in horses. The present invention further relates to compositions and methods for alleviating pain associated with skeletal injuries in horses and to treating skeletal injuries in horses. The present invention also relates to compositions and methods for treating or preventing glucocorticoid-induced bone loss in horses.

BACKGROUND OF THE INVENTION

The horse industry in the U.S. produces goods and services valued at $25.3 billion in 1996 (American Horse Council, Washington, D.C.).

Skeletal injuries are a significant cause of death in performance horses, which are horses involved in activities such as racing, pacing, and other competitive events. The loss of a performance horse to such an injury can have a profound and far reaching effect. These injuries are not only distressing to the horse owners who often have a large emotional and financial commitment at stake, and also to spectators and other horse lovers. Furthermore, these injuries can also be extremely dangerous and even life threatening for jockeys, racers, and others.

In California alone, between 150 and 200 horses die or are euthanized each year as a result of catastrophic bone injury due to racing or training. See Estberg, et al., Preventative Vet. Med. 33: 159–170, 1998, which is incorporated by reference herein in its entirety. In addition to ethical and humane considerations, there is a very strong financial incentive to properly care for and prevent and reduce the risk or incidence of skeletal injuries in horses.

The performance horse, such as a racehorse, is an athlete capable of reaching and sustaining high training and racing speeds. Under these conditions, great demands are placed on the weight-bearing structures of the musculoskeletal system. Injuries can often occur abruptly during exercise. Injuries can also be caused by chronic skeletal damage incurred while training and performing or by skeletal atrophy due to nonexercise and forced stall rest. Skeletal atrophy and bone loss is characterized by conditions such as osteoporosis or osteopenia. These conditions are characterized by a decrease in bone mass density and by microarchitectural deterioration of bone tissue, with a consequent increase in bone fragility and susceptibility to fracture. These undesired skeletal changes can occur relatively rapidly after only a few weeks of inactivity and raises concerns about the common practice of stall rest such as the housing of yearling horses in stalls prior to yearling sales or prior to the commencement of training. Furthermore, the necessity of submitting injured or sick horses to forced stall rest raises concerns about how best to return such horses to activity without causing injury.

Normal bone physiology involves a process wherein bone tissue is continuously being turned over by the processes of modeling and remodeling. In other words, there is normally an appropriate balance between resorption of existing bone tissue and the formation of new bone tissue. The exact mechanism underlying the coupling between bone resorption and formation is still unknown. However, an imbalance in these processes is manifested in various disease states and conditions of the skeleton.

Two different types of cells called osteoblasts and osteoclasts are involved in the bone formation and resorption processes, respectively. See H. Fleisch, *Bisphosphonates In Bone Disease, From The Laboratory To The Patient*, 4th Edition, Parthenon Publishing (2000), which is incorporated by reference herein in its entirety.

Studies from the California Racetrack necroscopy studies indicate that fatal catastrophic musculoskeletal injuries in horses, principally fractures of proximal seamoid, third metacarpus and humerus, occur at an incidence of 1.7 per 1000 starts. See Estberg, L. et al., "Fatal musculoskeletal injuries incurred during racing and training in thoroughbreds", *Journal of the American Veterinary Medical Association*, 208(1): 92–96 (Jan. 1, 1996), which is incorporated by reference herein in its entirety. This is in general agreement with data from other studies (New York 1.1 per 1000 starts; Minnesota and Illinois-1.8; Japan-3.2; Kentucky-1.4, South Africa 1.4; Australia 0.3) cited by Mundy, Proc. Annual Conference of American Association of Equine Practioners, 204–220 (1997), which is also incorporated by reference herein in its entirety. The incidence of non-fatal injuries, horses which develop an abnormal gait or which require the ambulance to attend to a horse occur at rates 3–7 times higher than these catastrophic injuries.

Horses returning to racing following a lay-up (spelling) period, greater than 60 days without a race or fast time work, are 70 times more likely to suffer a fatal humeral fracture. Sixty-five percent of these incidents occur within 10 days of a lay-up. It is speculated that the spelling period predisposes the horses to disuse osteoporotic change to these long bones Carrier et al. 1998.

Buckingham, S. H. W. et al., "Osteopenic effects of forelimb immobilization in horses", *Veterinary Record*, 128: 370–373 (1991), which is incorporated by reference herein in its entirety, demonstrated that immobilization of a forelimb of horses by applying a cast for 8 weeks caused loss of bone strength and mineral content from both limbs but was more pronounced in the leg with the cast.

The following references, which are all incorporated by reference herein in their entirety, provide additional background on the subject of skeletal injuries of horses:

Porr, C. A. et al., "Deconditioning Reduces Mineral Content of the Third Metacarpal Bone in Horses", *Journal of Animal Science*, 76: 1875–1879 (1998).

Johnson, B. J. et al., "Causes of death in racehorses over a 2 year period", *Equine Veterinary Journal*, 26(4): 327–330 (1994).

Estberg, L. et al., "Relationship between race start characteristics and risk of catastrophic injury in thoroughbreds: 78 cases (1992)", *Journal of the American Veterinary Medical Association*, 212(4): 544–549 (Feb. 15, 1998).

Hoekstra, K. E. et al., "Stalling Young Horses Alters Normal Bone Growth", *Association for Equine Sports Medicine Proceedings*, AGM, Leesburg, Va. (1998).

Carrier, T. K. et al., "Association between long periods without high-speed workouts and risk of complete humeral or pelvic fracture in thoroughbred racehorses; 54 cases (1991–1994)", *Journal of the American Veterinary Medical Association*, 212(10): 1582–1587 (May 15, 1998).

Estberg, L. et al., "High-speed exercise history and catastrophic racing fracture in thoroughbreds", *American Journal of Veterinary Research,* 57(11):1549–1555 (Nov. 1996).

Lepage, O. M. et al., "L'emploi d'un bisphosphonate (APD) dans la prevention des exoxtoses chez le poney Shetland. Eutde preliminaire. *Ann Med. Vet.,* 132:391–399 (1988).

Lepage, O. M. et al., "Aspects microradiographiques et en microscopie de fluorescence d'une exotose experimentale du metacarpein chez le poney Shetland et de son traitement par un bisphosphonate, L"AhpfBP (APD). Applications possible aucheval d'arme",*Annales Medicinae Militaris Belgicase* 3(2):38–44 (1989).

Estberg, L. et al., "A cross over study of intensive racing and training schedules and risk of catastrophic musculoskeletal injury and lay-up in California thoroughbred racehorses", *Preventative Vet. Med.,* 33: 159–170 (1998).

The skeletal injuries and underlying predisposing conditions are to be distinguished from navicular disease in horses. The navicular bone is a boat-shaped bone located at the medial side of the tarsus. Navicular disease is a specific disorder of this bone, causing lameness and frequently leading to loss of function in a performance horse. Without being limited by theory, the pathophysiology of this disease is not well defined but it is thought to be related to blood circulation through the foot and particularly to the navicular bone. Disruption to this blood supply leads to physical changes in the bone, causing pain. Navicular disease is a specific condition, affecting this bone only, and there is no evidence that circumstances which cause generalized bone resorption predispose to the development of navicular disease. PCT patent application number WO 97/12619, to Novartis, published Apr. 10, 1997 describes the use of various bisphosphonates in the treatment of navicular disease in horses. However, there is no teaching of the methods of the present invention. In contrast the present invention relates to composition and methods for preventing or reducing the risk of incidence of skeletal injuries in horses, i.e. conditions relating to abnormal or undesired changes in the bone resorption/formation balance, rather than to circulatory disorders associated with one specific bone.

Currently, there is no totally satisfactory means for preventing or reducing the risk or incidence of skeletal injuries in horses, nor to alleviating pain associated with skeletal injuries or to treating skeletal injuries.

Bisphosphonates are known in the art to bond to hydroxyapatite in bone and to inhibit the bone resorptive activity of osteoclasts. See H. Fleisch, Id. For example, bisphosphonates are known to be useful in the treatment of such diseases as osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation. Even though bisphosphonates have been used to treat the above-mentioned diseases, there is little evidence of their use for preventing or reducing the risk or incidence of skeletal injuries in horses or for alleviating pain associated with skeletal injuries or for treating skeletal injuries. At most there is the methods associated with the localized specific condition of navicular disease. Also, there are the specific limited studies on Shetland ponies where a bisphosphonate was used to reduce the size of exostoses induced by an experimental surgical lifting of the periosteum. Without being limited by theory, this application of a bisphosphonate falls outside the present discovery since the development of exostosis in response to a periosteal injury is not a disease/injury resulting from excessive bone resorption.

In addition to the above discussion, it is well-known that glucocorticoid use can result in bone loss in humans. These powerful drugs, such as prednisone or dexamethasone, are commonly used to treat the pain and inflammation associated with the activities of high performance horses. There is strong evidence that the use of these drugs in such horses can lead to bone loss and accompanying complications. There is thus a need to treat or prevent glucorticoid bone-loss, and its attendend conditions such as osteopenia and osteoporosis in horses.

It is surprisingly been found in the present invention that bisphosphonates are effective for preventing or reducing the risk or incidence of skeletal injuries in horses and for alleviating pain associated with skeletal injuries and for treating skeletal injuries.

It is an object of the present invention to provide a method of preventing or reducing the risk or incidence of skeletal injuries in horses comprising administering a therapeutically effective amount of a bisphosphonate or a pharmaceutically acceptable salt thereof or ester thereof or mixtures thereof.

It is another object of the present invention to provide a method of alleviating pain associated with skeletal injuries in horses comprising administering a therapeutically effective amount of a bisphosphonate or a pharmaceutically acceptable salt thereof or ester thereof or mixtures thereof.

It is another object of the present invention to provide a method of treating skeletal injuries in horses comprising administering a therapeutically effective amount of a bisphosphonate or a pharmaceutically acceptable salt thereof or ester thereof or mixtures thereof.

It is another object of the present invention to provide a method of treating or preventing glucocorticoid-induced bone loss in horses comprising administering a therapeutically effective amount of a bisphosphonate or a pharmaceutically acceptable salt thereof or ester thereof or mixture thereof.

It is another object of the present invention to provide the use of a bisphosphonate or a pharmaceutically acceptable salt thereof or ester thereof or mixture thereof for preventing or reducing the risk or incidence of skeletal injuries in horses.

It is another object of the present invention to provide the use of a bisphosphonate or a pharmaceutically acceptable salt thereof or ester thereof or mixture thereof for alleviating pain associated with skeletal injuries in horses.

It is another object of the present invention to provide the use of a bisphosphonate or a pharmaceutically acceptable salt thereof or ester thereof or mixture thereof for treating skeletal injuries in horses.

It is another object of the present invention to provide the use of a bisphosphonate or a pharmaceutically acceptable salt thereof or ester thereof or mixture thereof for treating or preventing glucocorticoid-induced bone loss in horses.

It is another object of the present invention to provide the use of a bisphosphonate or a pharmaceutically acceptable salt thereof or ester thereof or mixture thereof in the manufacture of a medicament for preventing or reducing the risk or incidence of skeletal injuries in horses.

It is another object of the present invention to provide the use of a bisphosphonate or a pharmaceutically acceptable salt thereof or ester thereof or mixture thereof in the manufacture of a medicament for alleviating pain associated with skeletal injuries in horses.

It is another object of the present invention to provide the use of a bisphosphonate or a pharmaceutically acceptable salt thereof or ester thereof or mixture thereof in the manufacture of a medicament for treating skeletal injuries in horses.

It is another object of the present invention to provide the use of a bisphosphonate or a pharmaceutically acceptable salt thereof or ester thereof or mixture thereof in the manufacture of a medicament for treating or preventing glucocorticoid-induced bone loss in horses.

It is another object of the present invention to provide a pharmaceutical composition for preventing or reducing the risk or incidence of skeletal injuries in horses comprising a therapeutically effective amount of a bisphosphonate or a pharmaceutically acceptable salt thereof or ester thereof or mixture thereof.

It is another object of the present invention to provide a pharmaceutical composition for alleviating pain associated with skeletal injuries in horses comprising a therapeutically effective amount of a bisphosphonate or apharmaceutically acceptable salt thereof or ester thereof or mixture thereof.

It is another object of the present invention to provide a pharmaceutical composition for treating skeletal injuries in horses comprising a therapeutically effective amount of a bisphosphonate or a pharmaceutically acceptable salt thereof or ester thereof or mixture thereof.

It is another object of the present invention to provide pharmaceutical compositions for treating or preventing glucocorticoid-induced bone loss in horses comprising a therapeutically effective amount of a bisphosphonate or a pharmaceutically acceptable salt thereof or ester thereof or mixture thereof.

These and other objects will become readily apparent from the detailed description which follows.

SUMMARY OF THE INVENTION

The present invention relates to a method of preventing or reducing the risk or incidence of skeletal injuries in horses comprising administering a therapeutically effective amount of a bisphosphonate or a pharmaceutically acceptable salt thereof or ester thereof or mixtures thereof.

The present invention also relates to a method of alleviating pain associated with skeletal injuries in horses comprising administering a therapeutically effective amount of a bisphosphonate or a pharmaceutically acceptable salt thereof or ester thereof or mixture thereof.

The present invention also relates to a method for treating skeletal injuries in horses comprising administering a therapeutically effective amount of a bisphosphonate or a pharmaceutically acceptable salt thereof or ester thereof or mixture thereof.

The present invention also relates to a method for treating or preventing glucocorticoid-induced bone loss in horses comprising administering a therapeutically effective amount of a bisphosphonate or a pharmaceutically acceptable salt thereof or ester thereof or mixture thereof.

The present invention also relates to the use of a bisphosphonate or a pharmaceutically acceptable salt thereof or ester thereof or mixture thereof for preventing or reducing the risk or incidence of skeletal injuries in horses.

The present invention also relates to the use of a bisphosphonate or a pharmaceutically acceptable salt thereof or ester thereof or mixture thereof for alleviating pain associated with skeletal injuries in horses.

The present invention also relates to the use of a bisphosphonate or a pharmaceutically acceptable salt thereof or ester thereof or mixture thereof for treating skeletal injuries in horses.

The present invention also relates to the use of a bisphosphonate or a pharmaceutically acceptable salt thereof or ester thereof or mixture thereof for treating or preventing glucocorticoid-induced bone loss in horses.

The present invention also relates to the use of a bisphosphonate or a pharmaceutically acceptable salt thereof or ester thereof or mixture thereof in the manufacture of a medicament for preventing or reducing the risk or incidence of skeletal injuries in horses.

The present invention also relates to the use of a bisphosphonate or a pharmaceutically acceptable salt thereof or ester thereof or mixture thereof in the manufacture of a medicament for alleviating pain associated with skeletal injuries in horses.

The present invention also relates to the use of a bisphosphonate or a pharmaceutically acceptable salt thereof or ester thereof or mixture thereof in the manufacture of a medicament for treating or preventing glucocorticoid-induced bone loss in horses.

The present invention also relates to the use of a bisphosphonate or a pharmaceutically acceptable salt thereof or ester thereof or mixture thereof in the manufacture of a medicament for treating skeletal injuries in horses.

The present invention also relates to a pharmaceutical composition for preventing or reducing the risk or incidence of skeletal injuries in horses comprising a therapeutically effective amount of a bisphosphonate or a pharmaceutically acceptable salt thereof or ester thereof or mixture thereof.

The present invention also relates to a pharmaceutical composition for alleviating pain associated with skeletal injuries in horses comprising a therapeutically effective amount of a bisphosphonate or a pharmaceutically acceptable salt thereof or ester thereof or mixture thereof.

The present invention also relates to a pharmaceutical composition for treating or preventing glucocorticoid-induced bone loss in horses comprising a therapeutically effective amount of a bisphosphonate or a pharmaceutically acceptable salt thereof or ester thereof or mixture thereof.

The present invention also relates to a pharmaceutical composition for treating skeletal injuries in horses comprising a therapeutically effective amount of a bisphosphonate or a pharmaceutically acceptable salt thereof or ester thereof or mixture thereof.

All percentages and ratios used herein, unless otherwise indicated, are by weight. The invention hereof can comprise, consist of, or consist essentially of the essential as well as optional ingredients, components, and methods described herein.

DETAILED DESCRIPTION OF THE INVENTION

The present invention relates to compositions and methods for preventing or reducing the risk or incidence of skeletal injuries in horses. The present invention further relates to compositions and methods for alleviating pain associated with skeletal injuries in horses and to treating skeletal injuries in horses. The methods of the present invention comprise administering to the horse a therapeutically effective amount of a bisphosphonate, or a pharmaceutically effective amount thereof.

The term "preventing or reducing the risk or incidence of skeletal injuries" means to provide a therapeutic intervention in the subject so that an injury does not occur or such that the probability of it occurring is lessened.

The term "alleviating pain associated with skeletal injuries" means to reduce, ameliorate, or remove the pain associated with such an injury.

The term "treating skeletal injuries" means to provide a therapeutic intervention in a subject once an injury has occurred.

The term "therapeutically effective amount", as used herein, means that amount of the bisphosphonate compound, that will elicit the desired therapeutic effect or response when administered in accordance with the desired treatment regimen. A preferred therapeutically effective amount of the bisphosphonate is an amount which effectively prevents or reduces the risk or incidence of skeletal injuries in horses, or which alleviates pain associated with skeletal injuries in horses, or which treats skeletal injuries in horses.

The term "pharmaceutically acceptable" as used herein means that the salts and derivatives of the bisphosphonates have the same general pharmacological properties as the free acid form from which they are derived and are acceptable from a toxicity viewpoint.

The term "pharmaceutically acceptable salt", as used herein refers to non-toxic salts of the compounds useful in the instant invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Pharmaceutically acceptable salts also specifically include hydrates as well as the anhydrous forms.

The term "glucocorticoid-induce" bone loss is familiar to one of skill in the art and is used to indicate a decrease in bone mass and its often accompanying conditions such as osteopenia and osteoporosis. It is well known that glucocorticoids, such as e.g., prednisone, and other immunosuppressant drugs can induce or cause such bone loss and conditions.

The dosage regimen utilizing the compounds of the present invention is selected in accordance with a variety of factors including type, species, age, weight, sex and medical condition of the subject; the severity of the condition to be treated; the route of administration; the renal and hepatic function of the subject; and the particular compound or salt thereof employed. An ordinarily skilled veterinarian or clinician can readily determine and prescribe the effective amount of the drug required to treat or reduce the risk of contracting the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.01 to 5.0 mg/kg/day. The exact dose is determined by one of ordinary skill in the art based on the size of the subject animal, the severity of the condition to be treated to prevented, the bisphosphonate to be utilized, and the frequency of administration. An alternative dosing regimen which could provide enhanced convenience and potential gastrointestinal safety advantages would be to deliver the proportional cumulative daily oral dose about once every 3 to about 16 days, e.g., once-weekly, twice-weekly, biweekly, or twice monthly. See PCT application WO 99/04773, to Merck & Co., Inc., published Feb. 4, 1999, which is incorporated by reference herein in its entirety. For oral administration, the compositions are preferably provided in the form of tablets, pastes or feed additives containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Typical weekly dosages would be proportionately about 7 times larger. For intravenous or subcutaneous administration a stable, non-irritant solution of active ingredient in a suitable vehicle with concentrations ranging from 0.1 to 100 mg/ml is contemplated. These product forms can be given on a daily basis, or less frequently, such as from about once every 3 days to about once every 2 months. Again, the exact dosage is determined by one of ordinary skill in the art based on factors discussed above. Convenient intravenous or subcutaneous administrations are given about once every month. Furthermore, compounds of the present invention can be administered in intranasal form via use of suitable intranasal vehicles, or via transdermal routes, using those forms of transdermal delivery systems well known to those of ordinary skill in the art. To be administered in the form of a transdermal delivery system, the dosage administration can be an immediate single unit dose or can be a sustained release system.

For methods of the present invention, the bisphosphonate compound is continuously administered until the desired change in bone mass density is observed, or the pain associated with a skeletal injury is alleviated, or the skeletal injury is treated. Bone mass density is readily determined using standard measuring techniques and equipment commonly used in humans. For example, the speed of a sound wave through the bone can be used to assess bone density, or radiographic techniques can be used to assess bone density and morphology. Nonlimiting examples of administration periods can range from a single treatment to the remaining lifespan of the mammal, although more typical periods of administration would be during the period of stall rest or recuperation from a skeletal injury.

Bisphosphonates

The methods and compositions of the present invention comprise the administration of a bisphosphonate or a pharmaceutically acceptable salt thereof. The bisphosphonates of the present invention correspond to the chemical formula wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

A non-limiting class of structures useful in the instant invention are those in which A is selected from the group consisting of H, OH, and halogen, and X is selected from the group consisting of C1–C30 alkyl, C1–C30 substituted alkyl, halogen, and C1–C10 alkyl or phenyl substituted thio.

A non-limiting subclass of structures useful in the instant invention are those in which A is selected from the group consisting of H, OH, and C1, and X is selected from the group consisting of C1–C30 alkyl, C1–C30 substituted alkyl, C1, and chlorophenylthio.

A non-limiting example of the subclass of structures useful in the instant invention is when A is OH, X is a 3-aminopropyl moiety and n is zero, so that the resulting compound is a 4-amino-1,-hydroxybutylidene-1,1-bisphosphonate, i.e. alendronate.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1–C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and J. Org. Chem 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

A non-limiting class of bisphosphonates useful in the instant invention are selected from the group consisting of alendronate, cimadronate, clodronate, etidronate, ibandronate, minodronate, neridronate, olpadronate, pamidronate, piridronate, risedronate, tiludronate, zoledronate, pharmaceutically acceptable salts thereof, and mixtures thereof.

More preferred is alendronate, ibandronate, risedronate, pharmaceutically acceptable salts or esters thereof, and mixtures thereof.

A non-limiting subclass of the above-mentioned class useful in the instant case contains alendronate, pharmaceutically acceptable salts thereof, esters thereof and mixtures thereof.

A nonlimiting subclass of the above-mentioned class useful in the instant case is such that the pharmaceutically acceptable salts of alendronate are selected from the group consisting of sodium, potassium calcium, magnesium, and ammonium salts. In a further nonlimiting class the salts are sodium salts, nonlimiting examples of which include for example, the monosodium, disodium, trisodium, tetrasodium, and other higher salts. Such salts can also include noninteger ratios such as the 1.5 sodium salt, the 2.75 sodium, etc. Also, various hydrates including integer and non-integer hydrates, as well as anhydrous forms are contemplated as within the scope of the present invention.

A non-limiting example of the subclass is alendronate monosodium trihydrate.

In other embodiments, other preferred salts are the sodium salt of ibandronate, and risedronate monosodium hemi-pentahydrate (i.e. the 2.5 hydrate of the monosodium salt).

It is recognized that mixtures of two or more of the bisphosphonate actives can be utilized.

Pharmaceutical Compositions

The compounds of the present invention can be administered in such oral dosage forms as tablets, capsules (each of which includes sustained release or timed release formulations), pills, powders, granules, elixirs, tinctures, suspensions, syrups, pastes, gels, solutions, and emulsions. Likewise, they may also be administered in intravenous (bolus or infusion), intraperitoneal, nasal sprays, suppositories, tooth pastes (i.e. dentifrices which are also useful for cleansing the teeth), topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed.

Compositions useful in the present invention comprise a pharmaceutically effective amount of a bisphosphonate or a pharmaceutically acceptable salt thereof. The bisphosphonate is typically administered in admixture with suitable pharmaceutical diluents, excipients, or carriers, collectively referred to herein as "carrier materials", suitably selected with respect to oral administration, i.e. tablets, capsules, elixirs, syrups, effervescent compositions, powders, and the like, and consistent with conventional pharmaceutical practices. For example, for oral administration in the form of a tablet, capsule, or powder, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like; for oral administration in liquid form, e.g., elixirs and syrups, effervescent compositions, the oral drug components can be combined with any oral, non-toxic, pharmaceutically acceptable inert carrier such as ethanol, glycerol, water and the like. Moreover, when desired or necessary, suitable binders, lubricants, disintegrating agents, buffers, coatings, and coloring agents can also be incorporated. Suitable binders can include starch, gelatin, natural sugars such as glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. A tablet formulations for alendronate monosodium trihydrate and other bisphosphonates are described in U.S. Pat. No. 5,358,941, to Bechard et al, issued Oct. 25, 1994, and U.S. Pat. No. 5,681,590, to Bechard et al., issued Oct. 28, 1997, which are both incorporated by reference herein in its entirety. Oral liquid alendronate formulations are described in U.S. Pat. No. 5,462,932, to Brenner et al, issued Oct. 31, 1995, which is incorporated by reference herein in its entirety. Intravenous alendronate formulations are described in U.S. Pat. No. 5,780,455, to Brenner et al, issued Jul. 14, 1998, which is incorporated by reference herein in its entirety. The compounds used in the present method can also be coupled with soluble polymers as targetable drug carriers. Such polymers can include polyvinylpyrrolidone, pyran copolymer, polyhydroxylpropyl-methacrylamide, and the like.

The precise dosage of the bisphonate will vary with the dosing schedule, the oral potency of the particular bisphosphonate chosen, the age, size, sex and condition of the subject, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and other clinical studies. Generally, an appropriate amount of bisphosphonate is chosen to obtain the desired change in bone mass density, or until the pain associated with a skeletal injury is alleviated, or the skeletal injury has been successfully treated.

EXAMPLES

The following examples further describe and demonstrate embodiments within the scope of the present invention. The examples are given solely for the purpose of illustration and are not to be construed as limitations of the present invention as many variations thereof are possible without departing from the spirit and scope of the invention.

EXAMPLES OF PHARMACEUTICAL COMPOSITIONS

Pharmaceutical Tablet Compositions

Tablets are prepared using standard mixing and formation techniques as described in U.S. Pat. No. 5,358,941, to Bechard et al., issued Oct. 25, 1994, which is incorporated by reference herein in its entirety.

Tablets containing about 10 mg of alendronate monosodium trihydrate, on an alendronic acid active basis are prepared using the following relative weights of ingredients.

| Ingredient | Per Tablets | Per 4000 Tablets |
|---|---|---|
| Alendronate Monosodium Trihydrate | 13.051 mg | 52.20 g |
| Anhydrous Lactose, NF | 71.32 mg | 285.28 g |
| Microcrystalline Cellulose, NF | 80.0 mg | 320.0 g |
| Magnesium Stearate, NF | 1.0 mg | 4.0 g |
| Croscarmellose Sodium, NF | 2.0 mg | 8.0 g |

The resulting tablets are useful for administration in accordance with the methods of the present invention, i.e. for preventing or reducing the risk or incidence of skeletal injuries in horses, or for alleviating pain associated with skeletal injuries in horses, or for treating skeletal injuries in horses.

Similarly, tablets comprising other relative weights of alendronate, on an alendronic acid active weight basis are prepared.

Also, tablets containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, tablets containing combinations of bisphosphonates are similarly prepared.

| Suspensions | |
|---|---|
| Ingredient | Percent W/W |
| Alendronate Monosodium Trihydrate | 1.3% w/w |
| Colloidal Silicon dioxide | 3.0 |
| Alpha-tocopherol | 0.2 |
| Fish Oil | 95.5 |

The resulting suspensions are useful for administration in accordance with the methods of the present invention.

Similarly, suspensions comprising other relative weights of alendronate, on an alendronic acid active weight basis are prepared.

Also, suspensions containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, tablets containing combinations of bisphosphonates are similarly prepared. In addition, suspensions containing combinations of bisphosphonates are similarly prepared.

| Solutions | |
|---|---|
| Ingredient | Percent W/V |
| A. | |
| Alendronate Monosodium Trihydrate | 1.3% w/v |
| Citric Acid | 1.0 |
| Sodium Citrate | 0.5 |
| Butterscotch Flavor | 0.2 |
| Purified Water | 97.0 |
| B. | |
| Alendronate Monosodium Trihydrate | 0.4% w/v |
| Sodium Carbonate | 0.7 |
| Sodium Bicarbonate | 0.6 |
| Tuna Water | 90.0 |
| Purified Water | 8.3 |

The resulting solutions are useful for administration in accordance with the methods of the present invention.

Similarly, solutions comprising other relative weights of alendronate, on an alendronic acid active weight basis are prepared.

Also, solutions containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, solutions containing combinations of bisphosphonates are similarly prepared.

| Ointments | |
|---|---|
| Ingredient | Percent W/W |
| Alendronate Monosodium Trihydrate | 1.3% w/w |
| Lecithin | 3.0 |
| Malt Syrup | 45.0 |
| White Petrolatum | 50.7 |

The resulting ointments are useful for administration in accordance with the methods of the present invention.

Similarly, ointments comprising other relative weights of alendronate, on an alendronic acid active weight basis are prepared.

Also, ointments containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, ointments containing combinations of bisphosphonates are similarly prepared.

| Gels | |
|---|---|
| Ingredient | Percent W/W |
| Alendronate Monosodium Trihydrate | 1.3% w/w |
| Citric Acid | 1.0 |
| Sodium Citrate | 0.5 |
| Poloxamer | 20.0 |

Gels (continued)

| Ingredient | Percent W/W |
| --- | --- |
| Propylene Glycol | 20.0 |
| Benzyl Alcohol | 2.0 |
| Purified Water | 57.0 |

The resulting gels are useful for administration in accordance with the methods of the present invention.

Similarly, gels comprising other relative weights of alendronate, on an alendronic acid active weight basis are prepared.

Also, gels containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, gels containing combinations of bisphosphonates are similarly prepared.

Pastes

| Ingredient | Percent W/W |
| --- | --- |
| Alendronate Monosodium Trihydrate | 1.3% w/w |
| Sodium Carboxymethylcellulose | 2.0 |
| Magnesium aluminum Silicate | 2.0 |
| Methyl paraben | 0.18 |
| Propyl Paraben | 0.02 |
| Sorbitol Solution | 20.0 |
| Propylene Glycol | 20.0 |
| Purified Water | 54.5 |

The resulting pastes are useful for administration in accordance with the methods of the present invention (e.g., as a dentifrice).

Similarly, pastes comprising other relative weights of alendronate, on an alendronic acid active weight basis are prepared.

Also, pastes containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, pastes containing combinations of bisphosphonates are similarly prepared.

Composition For Transdermal Delivery

| Ingredient | Percent W/V |
| --- | --- |
| Alendronate Monosodium Trihydrate | 1.3% w/v |
| Butylated Hydroxyanisole | 0.02 |
| Polysorbate 80 | 3.0 |
| Diethyleneglycol monobutyl ether | 5.0 |
| n-Methylpyrrolidone | 90.7 |

The resulting composition is useful for administration in accordance with the methods of the present invention.

Similarly, a composition comprising other relative weights of alendronate, on an alendronic acid active weight basis are prepared.

Also, compositions containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, compositions containing combinations of bisphosphonates are similarly prepared.

Composition For Transdermal Delivery (Skin Patch)

| Ingredient | Percent W/W |
| --- | --- |
| Alendronate Base | 5.0% w/w |
| Alcohol | 15.0 |
| Hydoxypropylcellulose | 1.0 |
| Mineral oil | 0.2 |
| Polyisobutylene | QSAD |
| Ethylenevinyl acetate | QSAD |

The resulting composition is useful for administration in accordance with the methods of the present invention.

Similarly, compositions comprising other relative weights of alendronate, on an alendronic acid active weight basis are prepared. Also, compositions containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, compositions containing combinations of bisphosphonates are similarly prepared.

Injectables (IV/IM, SC/IP)

| Ingredient | Percent W/V |
| --- | --- |
| Alendronate Monosodium Trihydrate | 2.0% w/V |
| Sodium Citrate | 0.5 |
| Benzyl Alcohol | 2.0 |
| Edetate Sodium | 0.01 |
| Sodium Metabisulfite | 0.02 |
| Water for Injection | 95.5 |

The resulting injectables are useful for administration in accordance with the methods of the present invention.

Similarly, injectables comprising other relative weights of alendronate, on an alendronic acid active weight basis are prepared.

Also, injectables Also, compositions containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, injectables containing combinations of bisphosphonates are similarly prepared.

Compositions for Intra-Nasal Delivery

Compositions for Intra-Nasal Delivery

| Ingredient | Percent W/W |
| --- | --- |
| Alendronate Monosodium Trihydrate | 2.0% w/w |
| Carboxymethylcellulose sodium | 0.2 |
| Dextrose | 0.9 |

-continued

Compositions for Intra-Nasal Delivery

| Ingredient | Percent W/W |
| --- | --- |
| Benzylalkonium chloride | 0.01 |
| Polysorbate 80 | 3.0 |
| Hydrochloric acid | 0.01 |
| Purified Water | 93.9 |

The resulting composition is useful for administration in accordance with the methods of the present invention.

Similarly, compositions comprising other relative weights of alendronate, on an alendronic acid active weight basis are prepared.

Also, compositions containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, compositions containing combinations of bisphosphonates are similarly prepared.

Sustained-Release Tablets

| Ingredient | Percent W/W |
| --- | --- |
| Alendronate Monosodium Trihydrate | 1.3% w/w |
| Citric Acid | 1.0 |
| Sodium Citrate | 0.5 |
| Cellulosic Polymer | 1.0 |
| Corn Starch | 5.0 |
| Sodium Starch Glycolate | 5.0 |
| Titanium Dioxide | 0.5 |
| Vanillin | 0.5 |
| Hydrogenated Castor Oil | 6.0 |
| Povidone | 5.0 |
| Acetylated Monoglycerides | 1.0 |
| Microcrystalline Cellulose | 18.0 |
| Lactose | 55.2 |

The resulting tablets are useful for administration in accordance with the methods of the present invention.

Similarly, tablets comprising other relative weights of alendronate, on an alendronic acid active weight basis are prepared.

Also, tablets containing other bisphosphonates at appropriate active levels are similarly prepared: e.g., cimadronate, clodronate, tiludronate, etidronate, ibandronate, neridronate, olpadronate, risedronate, piridronate, pamidronate, zoledronate, and the pharmaceutically acceptable salts or esters thereof. In addition, tablets containing combinations of bisphosphonates are similarly prepared.

In addition to the ingredients exemplified above, formulations can also contain additional suitable buffers, colors, dispersants, flavors, stabilizers and preservatives as necessary.

Bisphosphate Use in Stall Rested Horses

Sixteen healthy thoroughbred horses are used to evaluate the efficacy of alendronate for preventing disuse osteopenia in pasture fit horses, i.e. horses which had been at pasture for at least 4 months and then were confined to stall rest for 56 days. The horses are either treated with alendronate injection [once weekly (once every seven days), once every 14 days, or once every 28 days] or with placebo (once weekly saline injection). Bone metabolism is monitored using standard techniques, i.e. serum assays to determine levels of markers of bone turnover, bone resorption and bone formation and ultrasound is used to assess changes in bone density. Confinement of the saline treated horses is found to cause increased bone turnover, markedly increased bone resorption, decreased new bone formation and a resultant drop in bone density. The alendronate treated hoses exhibit very rapidly reduced bone turnover, suppressed bone resorption, and after 56 days improved bone density relative to the saline treated controls.

Materials and Methods:

Sixteen healthy adult thoroughbred horses (eight mares and eight male castrates) which had previously been running at pasture for at least 4 months are used. From the first day of treatment the horses are confined to stall rest for a period of 56 days with access to good quality hay and water ad libitum.

The horses are randomly allocated to 4 treatment groups of four horses, each containing two mares and two male castrates. Serum samples are collected and ultrasound measurements are taken on three occasions directly before commencement of stall rest. Assays are conducted on the serum samples to determine pre-confinement levels of C-telopeptides (C-Tx; a collagen breakdown product that is a marker of bone resorption); osteocalcin (a marker of bone turnover) and bone specific alkaline phosphatase (a marker of bone formation). Ultrasound is used to measure the speed of transmission of sound waves through the bone.

Group 1: Placebo, intravenous saline administered once weekly (once every seven days).

Group 2: 18.75 mg of alendronate monosodium trihydrate, on an alendronic acid active basis, in saline administered once weekly (once every seven days)

Group 3: 37.5 mg of alendronate monosodium trihydrate, on an alendronic acid active basis, in saline administered every fourteen days Group 4: 75 mg of alendronate monosodium trihydrate, on an alendronic acid active basis, in saline administered every 28 days Stall rest is commenced the day of first treatment. Serum samples are taken twice weekly and ultrasound measurements are taken each 14 days for the 56 days of the study to monitor changes in bone metabolism markers and in bone density relative to pre-confinement values. At the end of the study the horses are returned to the pasture.

Figure 1:
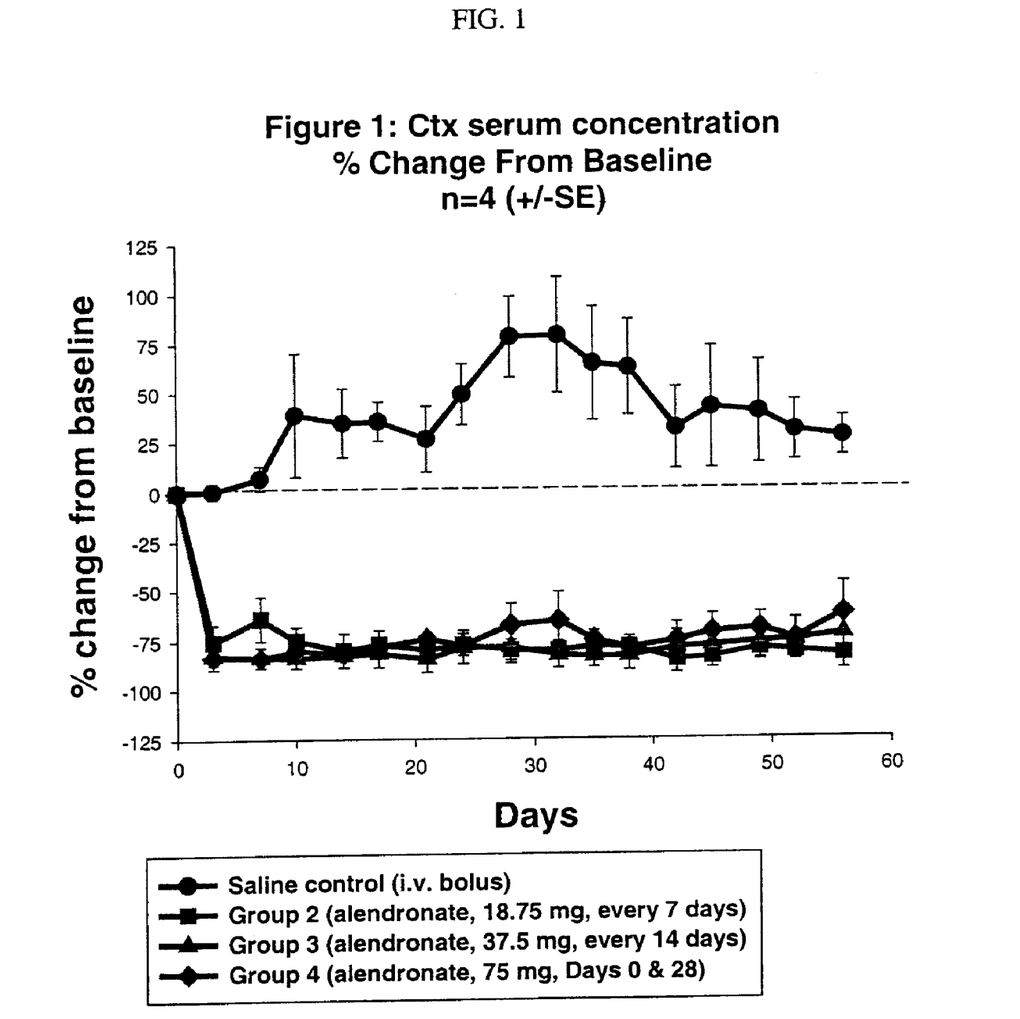
FIG. 1 is a graph showing the percentage change from baseline in C-telopeptides (i.e. C-Tx; a collagen breakdown product that is a marker of bone resorption) for a saline control group of horses, versus a group receiving 18.75 mg of alendronate monosodium trihydrate once every seven days, versus a group receiving 37.5 mg of alendronate monosodium trihydrate once every fourteen days, versus a group receiving 75 mg of alendronate monosodium trihydrate once every 28 days.

Results:

Intravenous alendronate is well tolerated by all horses with no adverse events detected. The marker of bone resorption (C-Tx) is found to increase to about 75% above baseline within one month after stall rest commenced in placebo treated horses, Group 1. In contrast this resorption marker is suppressed and remains about 75% below baseline in alendronate treated animals, Groups 2–4. See FIG. 1.

Figure 2:
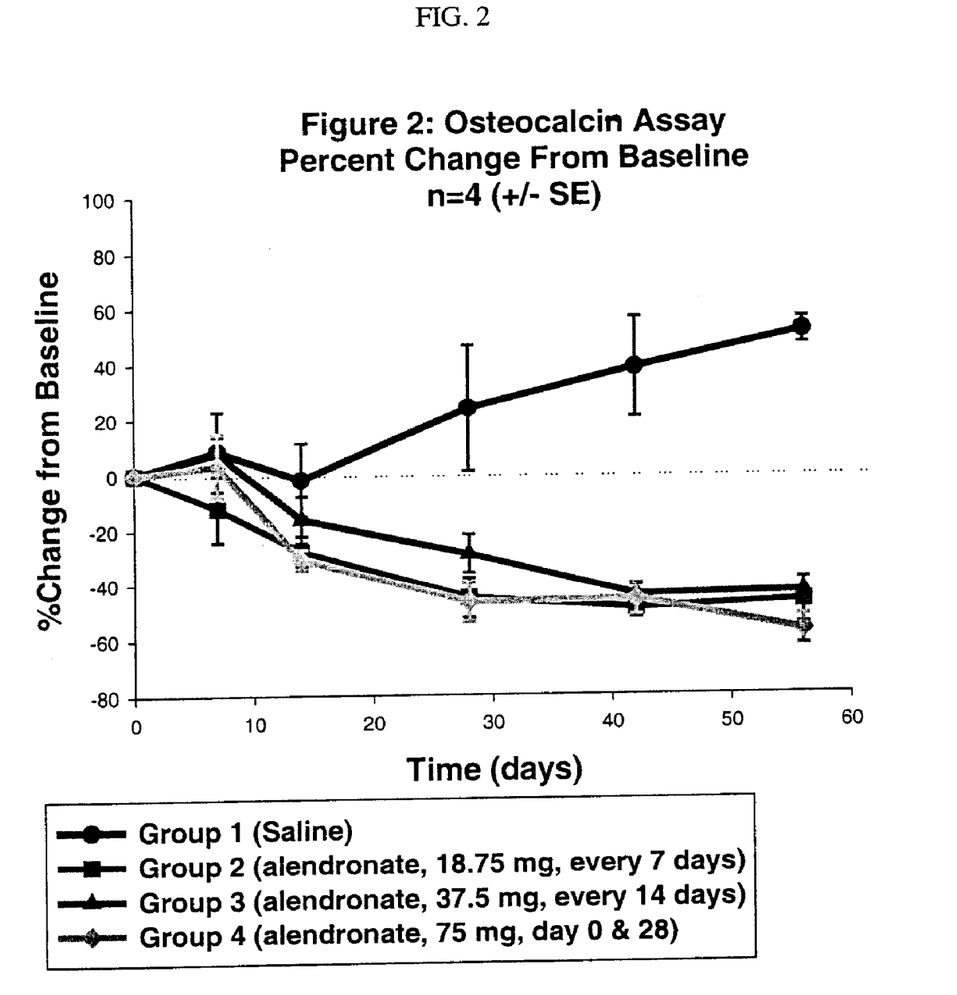
FIG. 2 is a graph showing the percentage change from baseline in osteocalcin (a marker of bone turnover) for a saline control group of horses, versus a group receiving 18.75 mg of alendronate monosodium trihydrate once every seven days, versus a group receiving 37.5 mg of alendronate monosodium trihydrate once every fourteen days, versus a group receiving 75 mg of alendronate monosodium trihydrate once every 28 days.

The marker for bone turnover (osteocalcin) increases over baseline in the placebo treated horses, Group 1, but is suppressed in the alendronate treated animals, Groups 2–4. See FIG. 2.

Figure 3:
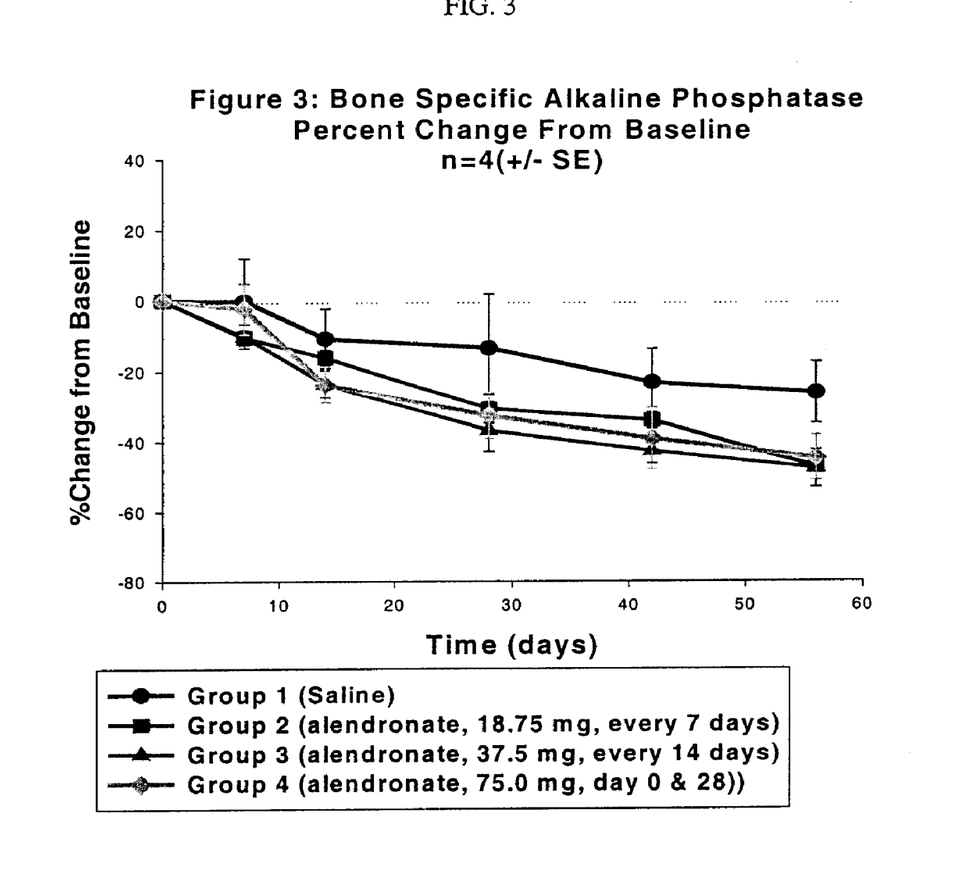
FIG. 3 is a graph showing the percentage change from baseline in bone specific alkaline phosphatase (a marker of bone formation) for a saline control group of horses, versus a group receiving 18.75 mg of alendronate monosodium trihydrate once every seven days, versus a group receiving 37.5 mg of alendronate monosodium trihydrate once every fourteen days, versus a group receiving 75 mg of alendronate monosodium trihydrate once every 28 days.

The marker for bone formation (bone specific alkaline phosphatase) is reduced in both placebo, Group 1, and alendronate treated horses, Groups 2–4. See FIG. 3.

Figure 4:
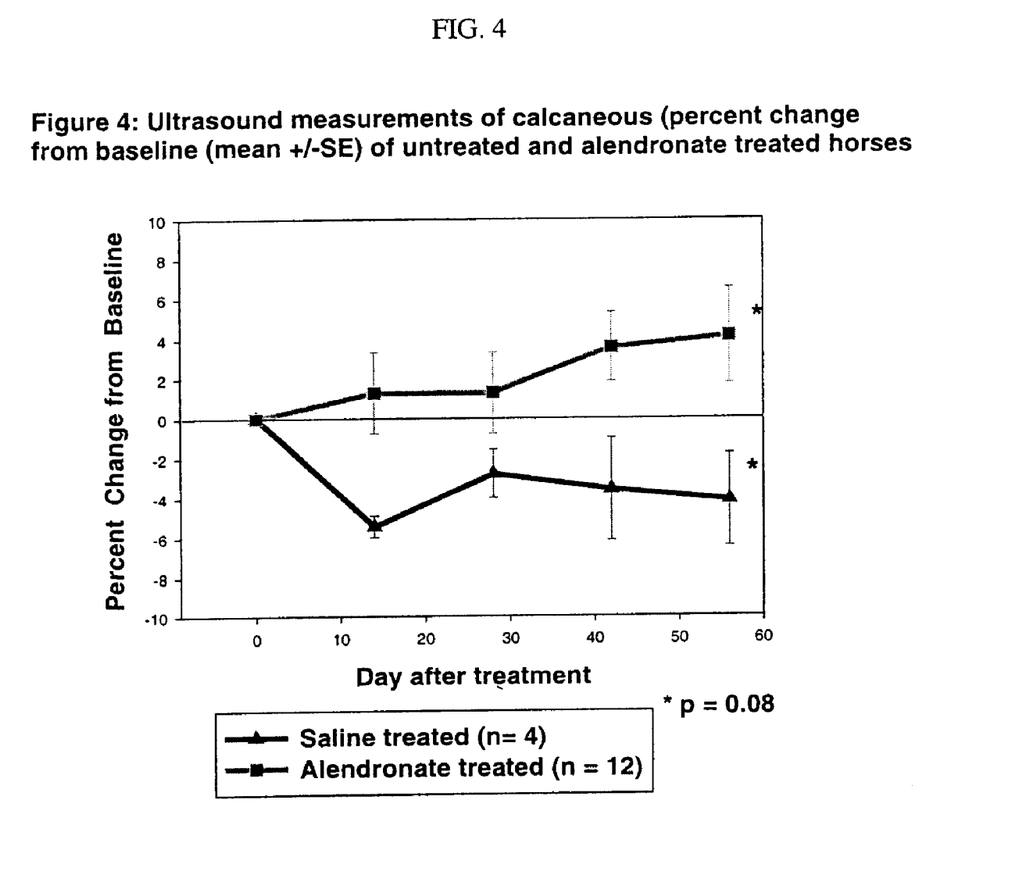
FIG. 4 is a graph showing the percentage change from baseline in ultrasound wave transmission speed in the calcaneus for a saline control group of horses versus a combined group receiving 18.75 mg of alendronate monosodium trihydrate once every seven days, or 37.5 mg of alendronate monosodium trihydrate once every fourteen days, or 75 mg of alendronate monosodium trihydrate once every 28 days.

Treatment with alendronate alters the apparent density of the calcaneus in stall rested horses as measured by the speed of transmission of ultrasound waves through the bone in the treated horses, Groups 2–4, compared to placebo treated horses. See FIG. 4. A decrease in transmission speed is consistent with a drop in bone density.

These data indicate that when healthy horses are deprived of normal exercise by being confined to a stall they rapidly increase the rate of bone resorption, reduce new bone formation and increase the rate of bone turnover. In addition there is a trend towards a reduction in bone density as assessed by ultrasound measurements of bone. Treatment with a bisphosphonate such as alendronate suppress the increase in bone resorption, reduces bone turnover, and provides an increase in bone density.

What is claimed is:

1. A method of preventing or reducing the risk or incidence of skeletal atrophy due to forced stall rest in horses comprising administering a therapeutically effective amount of a bisphosphonate or a pharmaceutically acceptable salt thereof or ester thereof or mixtures thereof.

2. The method of claim 1 wherein said bisphosphonate corresponds to the chemical structure wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring; and the pharmaceutically acceptable salts thereof and esters thereof.

3. The method of claim 1 wherein said bisphosphonate is selected from the group consisting of alendronate, cimadronate, clodronate, tiludronate, etidronate, ibandronate, neridronate, olpadronate, risedronate, piridronate, pamidronate, zoledronate, pharmaceutically acceptable salts thereof, esters thereof, and mixtures thereof.

4. The method of claim 3 wherein said bisphosphonate is alendronate, pharmaceutically acceptable salts thereof, esters thereof, and mixtures thereof.

5. The method of claim 4 wherein said pharmaceutically acceptable salt is selected from the group consisting of sodium, potassium calcium, magnesium, and ammonium salts.

6. The method of claim 5 wherein said pharmaceutically acceptable salt is a sodium salt.

7. The method of claim 6 wherein said pharmaceutically acceptable salt is alendronate monosodium trihydrate.

8. A method of alleviating pain associated with skeletal atrophy due to forced stall rest in horses comprising administering a therapeutically effective amount of a bisphosphonate or a pharmaceutically acceptable salt thereof or ester thereof or mixtures thereof.

9. The method of claim 8 wherein said bisphosphonate corresponds to the chemical structure wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring; and the pharmaceutically acceptable salts thereof or esters thereof.

10. The method of claim 8 wherein said bisphosphonate is selected from the group consisting of alendronate, cimadronate, clodronate, tiludronate, etidronate, ibandronate, neridronate, olpadronate, risedronate, piridronate, pamidronate, zoledronate, pharmaceutically acceptable salts thereof, esters thereof, and mixtures thereof.

11. The method of claim 10 wherein said bisphosphonate is alendronate, pharmaceutically acceptable salts thereof, esters thereof, and mixtures thereof.

12. The method of claim 11 wherein said pharmaceutically acceptable salt is selected from the group consisting of sodium, potassium calcium, magnesium, and ammonium salts.

13. The method of claim 12 wherein said pharmaceutically acceptable salt is a sodium salt.

14. The method of claim 13 wherein said pharmaceutically acceptable salt is alendronate monosodium trihydrate.

15. A method for treating skeletal atrophy due to forced stall rest in horses comprising administering a therapeutically effective amount of a bisphosphonate or a pharmaceutically acceptable salt thereof or ester thereof or mixtures thereof.

16. The method of claim 15 wherein said bisphosphonate corresponds to the chemical structure wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring; and the pharmaceutically acceptable salts thereof, or esters thereof.

17. The method of claim 15 wherein said bisphosphonate is selected from the group consisting of alendronate, cimadronate, clodronate, tiludronate, etidronate, ibandronate, neridronate, olpadronate, risedronate, piridronate, pamidronate, zoledronate, pharmaceutically acceptable salts thereof, esters thereof, and mixtures thereof.

18. The method of claim 17 wherein said bisphosphonate is alendronate, pharmaceutically acceptable salts thereof, esters thereof, and mixtures thereof.

19. The method of claim 18 wherein said pharmaceutically acceptable salt is selected from the group consisting of sodium, potassium calcium, magnesium, and ammonium salts.

20. The method of claim 19 wherein said pharmaceutically acceptable salt is a sodium salt.

21. The method of claim 20 wherein said pharmaceutically acceptable salt is alendronate monosodium trihydrate.

22. A method of treating or preventing glucocorticoid induced bone loss in horses comprising administering about 0.01 to about 5.0 mg per kg of a therapeutically effective amount of a bisphosphonate or a pharmaceutically acceptable salt thereof or ester thereof or mixtures thereof.

* * * * *